(12) United States Patent
Omi et al.

(10) Patent No.: US 9,208,582 B2
(45) Date of Patent: Dec. 8, 2015

(54) IMAGE ANALYZING SYSTEM AND METHOD

(75) Inventors: Yasuo Omi, Tokyo (JP); Ryo Takagi, Tokyo (JP); Osamu Miyazaki, Tokyo (JP); Yoshiaki Sugaya, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 1778 days.

(21) Appl. No.: 12/092,528

(22) PCT Filed: Oct. 31, 2006

(86) PCT No.: PCT/JP2006/321707
§ 371 (c)(1),
(2), (4) Date: Aug. 21, 2009

(87) PCT Pub. No.: WO2007/052634
PCT Pub. Date: May 10, 2007

(65) Prior Publication Data
US 2009/0304242 A1 Dec. 10, 2009

(30) Foreign Application Priority Data
Nov. 2, 2005 (JP) .................. 2005-319957

(51) Int. Cl.
*G06K 9/00* (2006.01)
*G06T 7/60* (2006.01)
(Continued)

(52) U.S. Cl.
CPC ............... *G06T 7/608* (2013.01); *A61B 6/461* (2013.01); *A61B 6/469* (2013.01); *A61B 6/507* (2013.01);
(Continued)

(58) Field of Classification Search
USPC ......................................... 382/128
See application file for complete search history.

(56) References Cited

U.S. PATENT DOCUMENTS 5,262,945 A 11/1993 DeCarli et al.
7,454,053 B2 * 11/2008 Bryll et al. .................. 382/152
(Continued)

FOREIGN PATENT DOCUMENTS

EP 1372116 12/2003
JP 2002-109550 4/2002
(Continued)

OTHER PUBLICATIONS

Official communication from the European Patent Office in connection with counterpart European patent application No. 06822636.
(Continued)

*Primary Examiner* — Valerie Lubin
*Assistant Examiner* — Reginald R Reyes
(74) *Attorney, Agent, or Firm* — Cooper & Dunham LLP

(57) ABSTRACT

An image analysis system that analyzes an image of an object's organ having an anatomically symmetric shape includes:
an image data read means that reads image data of the organ,
a memory means that is connected to the image data read means, and stores the read image data,
a display means that is connected to the memory means, and displays the image data as an image,
a centerline setting means that is connected to the memory means, and sets a centerline of the organ in the image displayed on the display means,
a region-of-interest setting means that is connected to the memory means, and uses the centerline to set a plurality of or at least one pair of regions of interest at anatomically symmetric opposite positions in the image of the organ, and
an input means that is connected to the region-of-interest setting means, and inputs conditions for setting of the regions of interest in the image.

3 Claims, 16 Drawing Sheets

(51) Int. Cl.
   *A61B 6/00* (2006.01)
   *G06T 7/00* (2006.01)
   *A61B 6/03* (2006.01)

(52) U.S. Cl.
   CPC ............. *G06T 7/0012* (2013.01); *A61B 6/03* (2013.01); *A61B 6/501* (2013.01); *G06T 2207/30016* (2013.01)

(56) References Cited

U.S. PATENT DOCUMENTS

| | | | |
|---|---|---|---|
| 2002/0136437 A1* | 9/2002 | Gerard et al. | 382/128 |
| 2002/0196965 A1 | 12/2002 | Wallace et al. | |
| 2005/0058331 A1 | 3/2005 | Klotz | |
| 2005/0259849 A1* | 11/2005 | Pavlidis | 382/118 |
| 2005/0283070 A1 | 12/2005 | Imielinska et al. | |
| 2010/0274117 A1* | 10/2010 | Gunther et al. | 600/410 |

FOREIGN PATENT DOCUMENTS

| | | |
|---|---|---|
| JP | 2006-136506 | 6/2006 |
| WO | WO02/069799 | 9/2002 |

OTHER PUBLICATIONS

Tomandl, B. F. et al. (2003), "Comprehensive imaging of ischemic stroke with multisection CT", Radiographics, The Radiological Society of North America, US, vol. 23, No. 3, pp. 565-592.

Liu, X. et al. (2005), "A novel quantification method for determining previously undetected silent infarcts on MR-perfusion in patients following carotid endartectomy", Proc. SPIE, vol. 5747, pp. 796-804.

Imielinska, C. et al. (2005), "Toward Objective Quantification of Perfusion-weighted Computed Tomography in Subarachnoid Hemorrhage: Quantification of Symmetry and Automated Delineation of Vascular Territories<1>", Academic Radiology, Reston, VA, vol. 12, No. 7, pp. 874-887.

* cited by examiner

FIG.20

| LEFT-AND-RIGHT RATIO | GRADE | NUMBER OF ROIs | A × B |
|---|---|---|---|
| 0~10% | 5 | 1 | 5 |
| 10~20% | 4 | 2 | 8 |
| 20~30% | 3 | 0 | 0 |
| 30~40% | 2 | 1 | 2 |
| 40~50% | 1 | 1 | 1 |
| 50~100% | 0 | 4 | 0 |

→ SUM TOTAL: SERIOUSNESS OF BLOOD-FLOW ABNORMALITY

FIG.21

| ROI No. | Mean(L) | Mean(R) | SD(L) | SD(R) | MEAN RATIO (R/L) | MEAN DIFFERENCE (R-L) |
|---|---|---|---|---|---|---|
| 1 | xx.xx | xx.xx | xx.xx | xx.xx | xx.xx | xx.xx |
| 2 | xx.xx | xx.xx | xx.xx | xx.xx | xx.xx | xx.xx |
| 3 | xx.xx | xx.xx | xx.xx | xx.xx | xx.xx | xx.xx |
| 4 | xx.xx | xx.xx | xx.xx | xx.xx | xx.xx | xx.xx |
| 5 | xx.xx | xx.xx | xx.xx | xx.xx | xx.xx | xx.xx |
| 6 | xx.xx | xx.xx | xx.xx | xx.xx | xx.xx | xx.xx |
| 7 | xx.xx | xx.xx | xx.xx | xx.xx | xx.xx | xx.xx |
| 8 | xx.xx | xx.xx | xx.xx | xx.xx | xx.xx | xx.xx |

IMAGE ANALYZING SYSTEM AND METHOD

TECHNICAL FIELD

The present invention relates to an image analysis system and method, or more particularly, to an image analysis system and method preferably applied to image analysis of an anatomically symmetric organ.

BACKGROUND ART

As a technique for rendering a blood flow in a capillary of a tissue or in an equivalent functional vasculature, a technology relevant to a diagnosis support function for CT perfusion has been disclosed in non-patent document 1. Specifically, multiple ROIs are set in each of functional images obtained by performing CT perfusion. A difference of a mean value or a standard deviation of a blood-flow parameter (a cerebral blood flow (CBF), a cerebral blood volume (CBV), or a mean transit time (MTT)) within each of the ROIs is assessed in order to determine whether an object part (ROI) is an affected part.

Non-patent document 1: "Development of CT perfusion diagnosis support function (multi transparency view)" (journal of Japanese Society of Radiological Technology, Vol. 59, No. 9, p. 1032&22)

However, the present inventor et al. have noticed a problem, which will be described below, as a result of discussion on the prior art. Specifically, in the related art 1, ROIs are manually set. At this time, subject is reflected on setting of ROIs. Unless the ROIs are accurately disposed, the results of analysis are likely to be erroneous.

DISCLOSURE OF THE INVENTION

An object of the invention is to provide an image analysis system and method capable of accurately designating ROIs.

According to the invention, an image analysis system that analyzes an image of an organ of an object to be examined having an anatomically symmetric shape includes: an image data read means that reads image data of the organ; a memory means that is connected to the image data read means and stores the read image data; a display means that is connected to the memory means and displays the image data as an image; a centerline setting means that is connected to the memory means and sets a centerline of the organ in the image displayed on the display means; a region-of-interest setting means that is connected to the memory means and uses the centerline to set multiple or at least one pair of regions of interest at anatomically symmetrical positions in the image of the organ; an input means that is connected to the region-of-interest setting means and inputs conditions for designating the regions of interest in the image; a region-of-interest analysis means that is connected to the memory means, obtains an analytic value of image data in each of the multiple regions of interest set in the image, and stores the analytic value in the memory means; and an assessment means that is connected to the memory means and assesses the state of the object according to a degree of a difference in the analytic value between the regions of interest disposed at the opposite positions.

Moreover, according to the invention, an image analysis method for analyzing an image of an object's organ having an anatomically symmetric shape includes: (1) a step of designating a centerline of the organ in the image; (2) a step of using the centerline set at the step (1) to set parting lines; (3) a step of using the parting lines set at the step (2) to set multiple or one or more pairs of regions of interest at symmetrically opposite positions; (4) a step of using image data in each of the regions of interest set at the step (3) to obtain an analytic value of image data in each of the regions of interest; and (5) a step of assessing the state of the object according to a degree of a difference in the analytic value between the opposite regions of interest.

BRIEF DESCRIPTION OF THE DRAWINGS

FIG. 20 is a diagram showing another example of display of the results of assessment in an embodiment 3; and FIG. 21 is a diagram showing an example of display for comparing analytic values of ROIs, which are located at anatomically symmetric positions, with each other in an embodiment 4.

BEST MODE FOR CARRYING OUT THE INVENTION

Embodiments of the invention will be described below in conjunction with the drawings.

Embodiment 1

Figure 1:
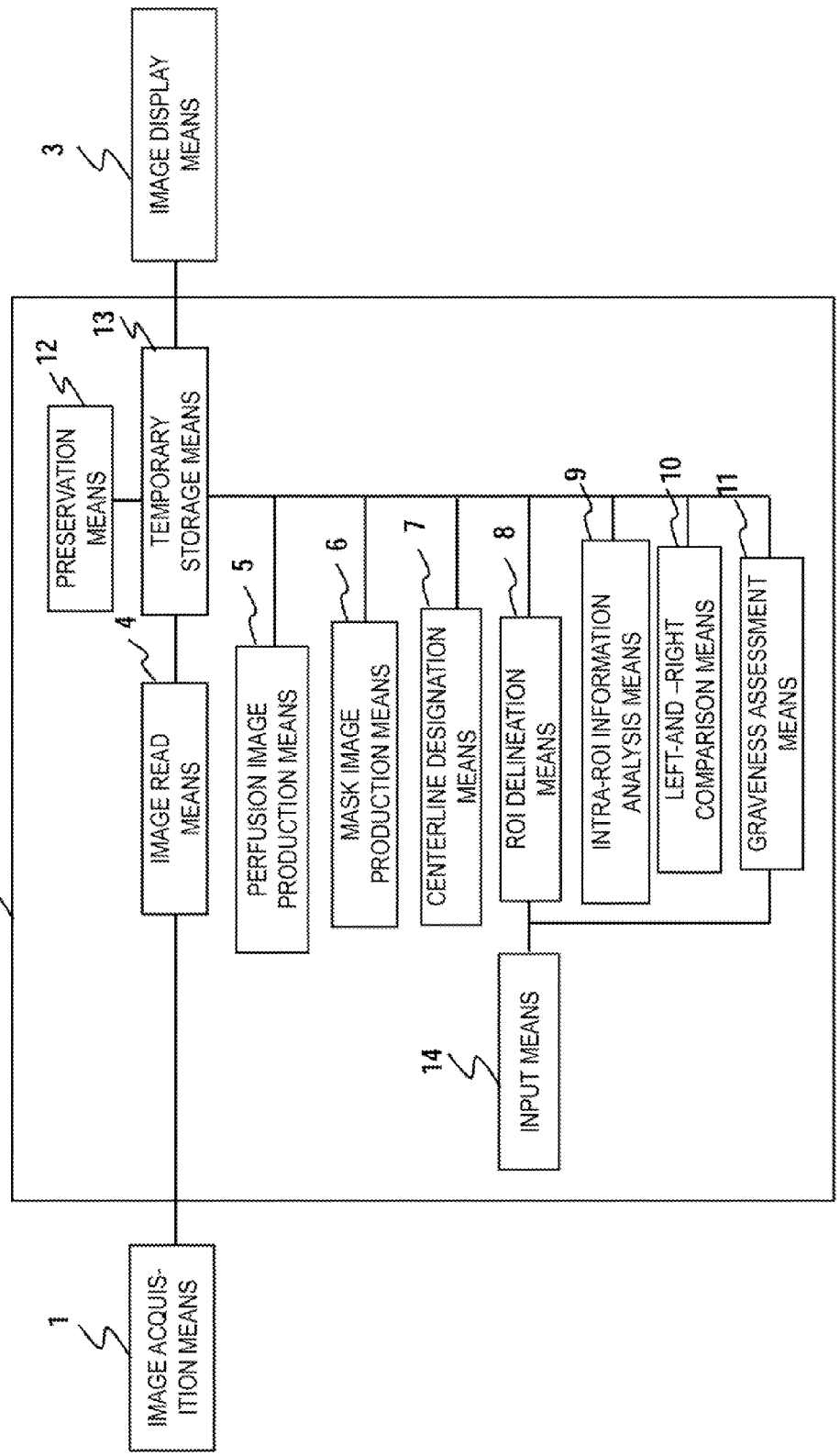
FIG. 1 is a block diagram showing an overall configuration of an image analysis system in accordance with the invention.

FIG. 1 is a block diagram showing an overall configuration of an image analysis system constituting the invention. Noted is that the present embodiment is concerned with a case where an object's head (an image of the brain) is imaged by an X-ray CT apparatus or the like in order to construct a perfusion image thereof for the purpose of analyzing the cerebral function.

As shown in FIG. 1, the image analysis system mainly includes an image acquisition means 1, an arithmetic processing means 2, and an image display means 3. The image acquisition means 1 is an acquisition apparatus for medical-purpose digital image data of an X-ray CT image, an MR image, an X-ray image, or the like, that is, a medical-purpose image diagnosis apparatus such as an X-ray CT apparatus, an MRI apparatus, or an X-ray imaging apparatus. The arithmetic processing means 2 is a computer integrated into the image acquisition means 1 or included externally therein. The arithmetic processing means 2 internally include some components.

Sequentially, reference numeral 4 denotes an image read means that reads a raw image of medical-purpose digital image data (X-ray CT image, MR image, or X-ray image), and that is connected to a main unit of the image acquisition means 1 and also connected to a temporary storage means 13 that will be described later. The temporary storage means 13 is used to temporarily store images read from the image acquisition means 1.

Reference numeral 5 denotes a perfusion image construction means that is connected to the temporary storage means 13 and that performs arithmetic processing on original images stored in the temporary storage means 13 so as to construct a cerebral perfusion functional image (hereinafter, called a perfusion image, and will be detailed later).

Reference numeral 6 denotes a mask image construction means that is connected to the temporary storage means 13 and that performs arithmetic processing on a raw image or a perfusion image, which is stored in the temporary storage means 13, so as to construct a mask image that includes only a cerebral region in the raw images or perfusion image.

Reference numeral 7 denotes a centerline setting means that is connected to the temporary storage means 13 and that sets a centerline in the raw image or the brain image of the perfusion image which is stored in the temporary storage means 13.

Reference numeral 8 denotes an ROI delineation means that is connected to the temporary storage means 13 and an input means 14 to be described later, and that delineates ROIs in the raw image or perfusion image, which is stored in the temporary storage means 13, on the basis of setting parameters inputted from the input means 14.

Reference numeral 9 denotes an intra-ROI information analysis means that is connected to the temporary storage means and that analyzes information in each of ROIs delineated in a perfusion image stored in the temporary storage means 13 so as to calculate a mean value or a standard deviation, etc.

Reference numeral 10 denotes a left-and-right comparison means that is connected to the temporary storage means 13 and that compares mean values or standard deviations of perfusion image data items in ROIs, which are obtained by the intra-ROI information analysis means, with each other for ROIs disposed at anatomically laterally symmetrical positions to examine the degree of the difference.

Reference numeral 11 denotes a seriousness assessment means that is connected to the temporary storage means 13 and the input means 14 to be described later, and that assesses the seriousness of an object according to the parameters for assessment inputted using the input means 14 and the degrees of the differences obtained by the left-and-right comparison means 10.

Reference numeral 12 denotes a storage means, such as a hard disk, that is connected to the temporary storage means and that stores an image or the like, which is stored in the temporary storage means 13, for a prolonged period.

Reference numeral 13 denotes the temporary storage means that is connected to the pieces of means 4 to 12 or the like and also connected to the image display means 3, and that temporarily stores an image or the like read by the image read means 4, stores a progress of processing performed by each of the pieces of means 5 to 11, and allows the progress to be displayed on the image display means 3 so that the progress will be seen by an operator.

Reference numeral 14 denotes the input means such as a mouse, a keyboard, or the like that is used to input parameters to the ROI delineation means 8 or the seriousness assessment means 11 for delineating ROIs or for assessing seriousness.

Moreover, at least one of a digital signal processor (DSP), a micro processor unit (MPU), and a central processing unit (CPU) is included in the arithmetic processing means 2, though it is not shown. Moreover, the image read means 4, perfusion image construction means 5, mask image construction means 6, centerline setting means 7, ROI delineation means 8, intra-ROI information analysis means 9, left-and-right comparison means 10, and seriousness assessment means 11 are pieces of software or programs for accomplishing the respective purposes of use. The arithmetic processing means 2 includes other various pieces of arithmetic software or other various arithmetic programs that are not shown. The image display means 3 is a display device such as a display, and may be integrated with one or both of the image acquisition means 1 and arithmetic processing means 2 or may be independently installed.

Figure 2:
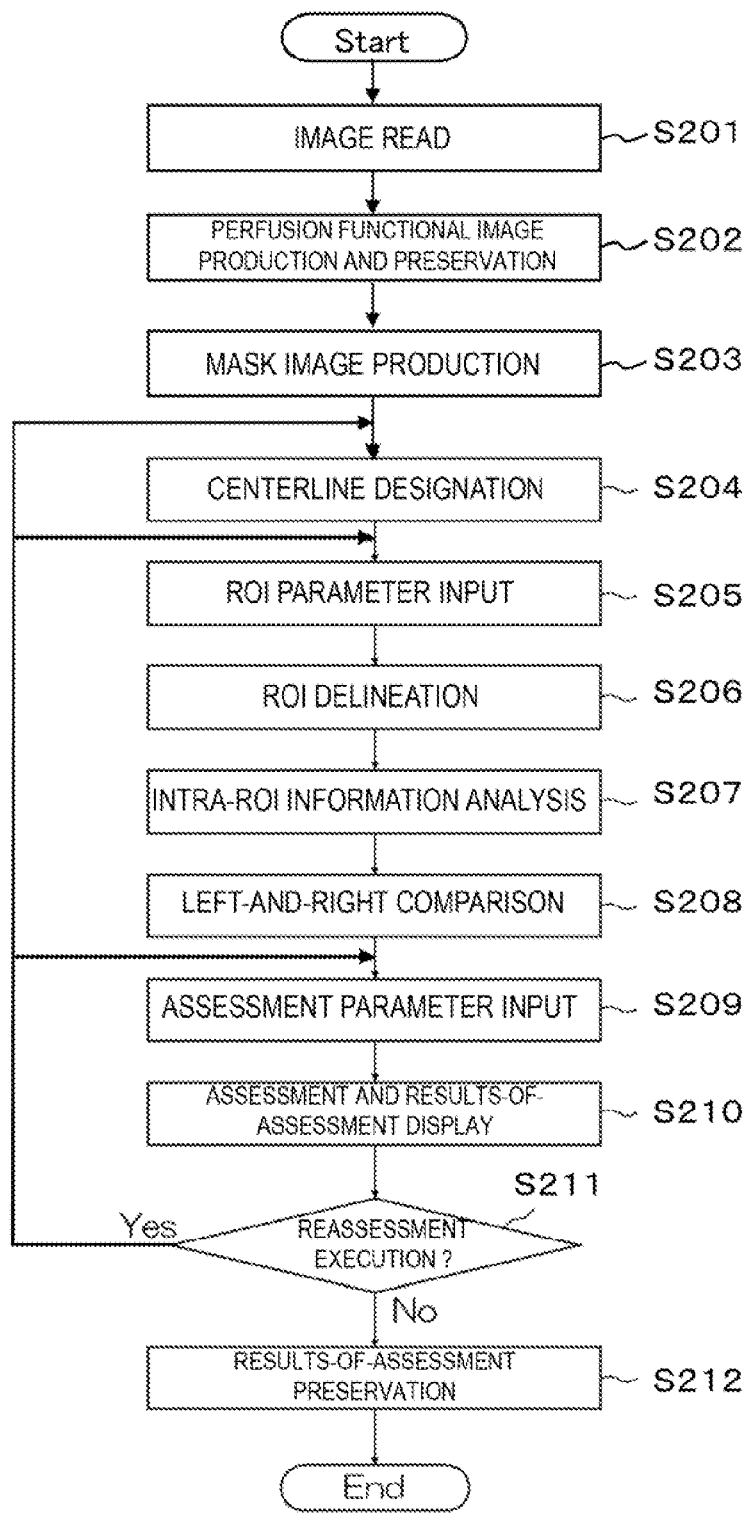
FIG. 2 is a flowchart expressing a flow of image analysis processing to be performed using the image analysis system in accordance with an embodiment 1 of the invention.

Next, a flow of image analysis processing to be performed using the image analysis system in accordance with the embodiment 1 of the invention will be described in conjunction with the flowchart of FIG. 2. Steps will be sequentially described below.

(Step 201)

First, the image read means 4 reads an image that is an object of processing (an X-ray CT image, MR image, X-ray image, or the like), and stores it in the temporary storage means 13. At this time, an image stored in advance in the storage means 12 may be read, or medical-purpose digital image data newly acquired by the image acquisition means 4 may be read.

(Step 202)

Thereafter, the perfusion image construction means 5 constructs a perfusion image on the basis of medical-purpose digital image data stored in the temporary storage means 13, and stores the perfusion image in the storage means 12 or temporary storage means 13. What is referred to as the perfusion image is an image constructed by imaging a blood flow in a capillary of a tissue or in an equivalent functional vasculature. A technique described in, for example, JP-A-2004-97665 is used to obtain a blood-flow parameter such as a cerebral blood flow (CBF), a cerebral blood volume (CBV), or a mean transit time (MTT), etc., and imaging is then performed.

(Step 203)

Thereafter, the mask image construction means 6 constructs a mask image for the perfusion image stored at step 202. What is referred to as the mask image is an image constructed by separating pixels, which have values other than zero, from pixels which have a value of zero (or nearly zero) and then replacing the pixels with specific values, for example, 1 and 0. A mask image construction procedure will be described below.

<Mask Image Construction Method>

Figure 3:
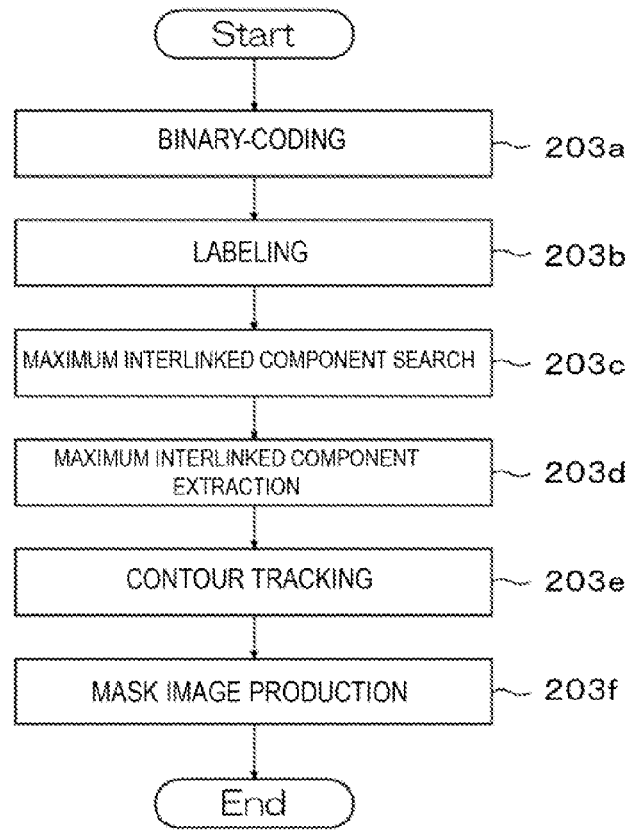
FIG. 3 is a flowchart presenting a mask image construction method.

To begin with, a mask image construction method at step 203 will be described below. FIG. 3 is a flowchart presenting the mask image construction method. A description will be made sequentially.

(Step 203*a*)

First, the perfusion image constructed at step 202 is binarized. Binarization is achieved by replacing pixels, which have pixel values equal to or larger than a threshold, with 1, and replacing pixels, which have pixel values falling below the threshold, with 0. The threshold at this step may be able to be externally inputted or may be stored as an initial value in advance in the system. For example, an arbitrary value making it possible to separate a living tissue that is an object of assessment from a living tissue adjoining the living tissue with room air created in the gap between them will do.

(Step 203*b*)

Thereafter, the image binarized at step 203*a* is subjected to labeling processing. What is referred to as labeling processing is to perform grouping by separating an object's head region, which is included in a part whose image is binarized at step 203*a* to reveal that the pixel values are equal to or larger than the threshold, from a table region, etc., for example. For example, when a head image is analyzed, grouping is performed to set the head region to a label value of 50 and the table region to a label value of 51.

(Step 203*c*)

Thereafter, maximum interlinked components (a part having the largest part) are searched from each part of an object or the like in the image having undergone labeling processing at step 203*b*. One of the labeled regions in the image to which a region that is an object of diagnosis refers is identified. For example, a concrete search algorithm scans an entire labeled image, performs the processing of counting the number of pixels for each of label values, and selects the label value, which is assigned to a large number of pixels, as a region of maximum interlinked components.

(Step 203*d*)

Thereafter, a part decided as the maximum interlinked components at step 203*c* is extracted. To be more specific, the maximum interlinked components alone are left intact at step 203*c*, and the other pixel values are replaced with 0. Consequently, when a table or the like is visualized in an image, it is deleted in order to construct an image in which the head region alone is shown.

(Step 203*e*)

Thereafter, the outline of the maximum interlinked components extracted at step 203*d* is tracked in order to extract the contour of the outermost circumference of the maximum interlinked components. As a concrete method for tracking and extracting a contour, for example, the image extracted at step 203*d* is sequentially scanned in a sideways direction from a pixel at the left upper corner of the image in order to first detect a pixel whose label value is not zero. With the detected pixel as a start point, the outline is tracked counterclockwise until tracking returns to the start point. Thus, the contour can be extracted. Further, the contour extracted at this step is replaced with a value, for example, 1 or the like different from the label values.

(Step 203*f*)

Figure 4:
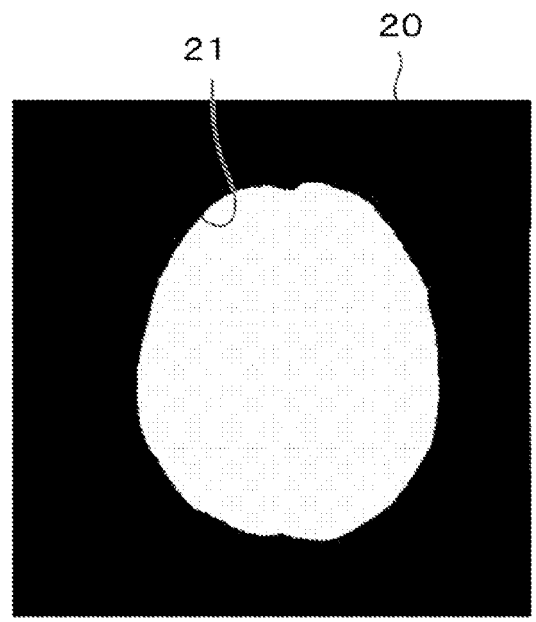
FIG. 4 is a view showing a constructed mask image.

Thereafter, the inside of the contour obtained at step 203*e* is painted out with a pixel value of 1 in order to construct a mask image 20 like the one shown in FIG. 4. In order to paint out the inside of a contour 21, a seed fill algorithm that is an algorithm for painting out the inside of a closed region with one point in the inside of the closed region as a start point can be applied.

(Step 204)

Thereafter, the centerline setting means 7 sets a centerline on the basis of the mask image obtained at step 203. A centerline setting method will be described below.

<Centerline Setting Method>

In centerline setting processing, first, based on the mask image constructed according to the technique described above, the position of a barycenter in a mask and the slope of a principal axis of inertia in a rigid body in a case where the mask is tentatively represented by the rigid body (one of orthogonal coordinate axes obtained when a tensor of inertia of a rigid body is diagonalized) are calculated. Assuming that I(x,y) denotes a pixel value at coordinates (x,y) in a mask image, the position (Xc,Yc) of the barycenter and the slope q of the principal axis of inertia can be worked out by calculating equations (1) and (2) presented below.

$$X_c = \sum_x \sum_y xI(x, y) \Big/ \sum_x \sum_y I(x, y) \quad \text{[Mathematics 1]}$$

$$Y_c = \sum_x \sum_y yI(x, y) \Big/ \sum_x \sum_y I(x, y)$$

$$\theta = \frac{1}{2}\tan^{-1}(b/a-c)$$

$$a = \sum_x \sum_y x^2 I(x, y) \Big/ \sum_x \sum_y I(x, y) - X_c^2 \quad \text{[Mathematics 2]}$$

$$b = 2\left(\sum_x \sum_y xyI(x, y) \Big/ \sum_x \sum_y I(x, y) - X_c Y_c\right)$$

$$c = \sum_x \sum_y y^2 I(x, y) \Big/ \sum_x \sum_y I(x, y) - Y_c^2$$

Figure 5:
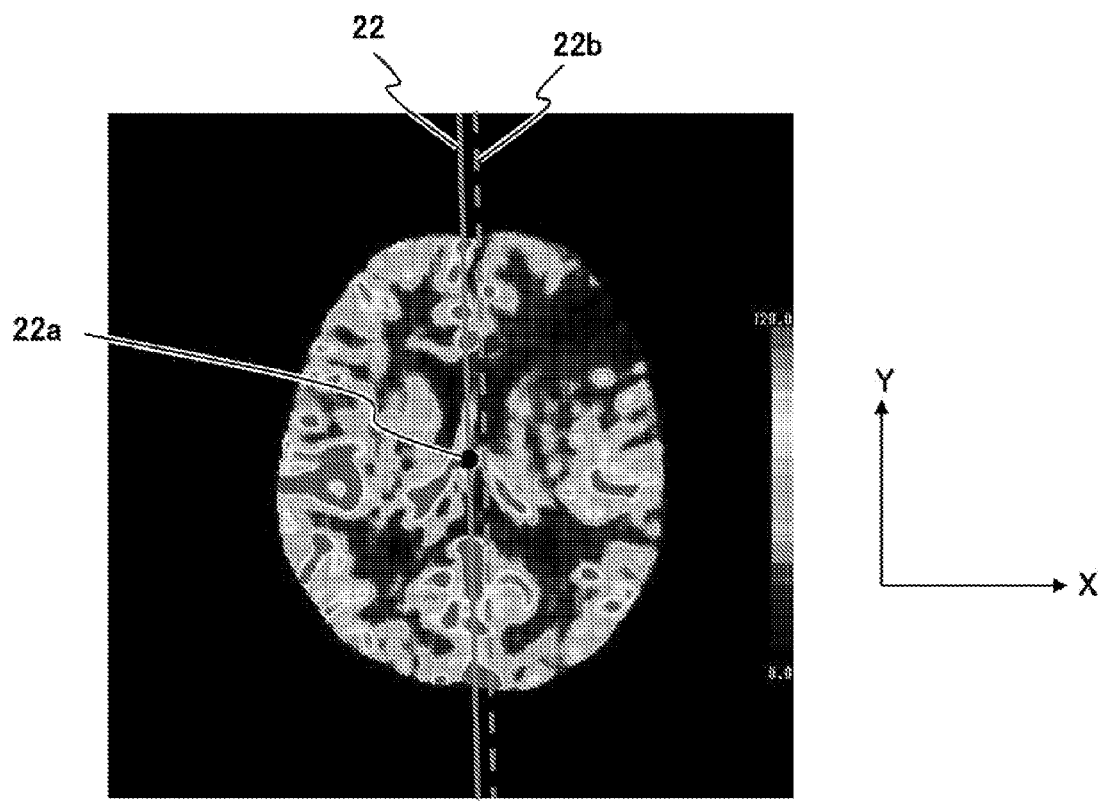
FIG. 5 is a view showing a scene where a centerline is drawn.

A straight line that passes the barycenter 22*a* and runs in parallel with the principal axis of inertia 22*b* is drawn, whereby a centerline 22 shown in FIG. 5 is obtained.

Figure 6:
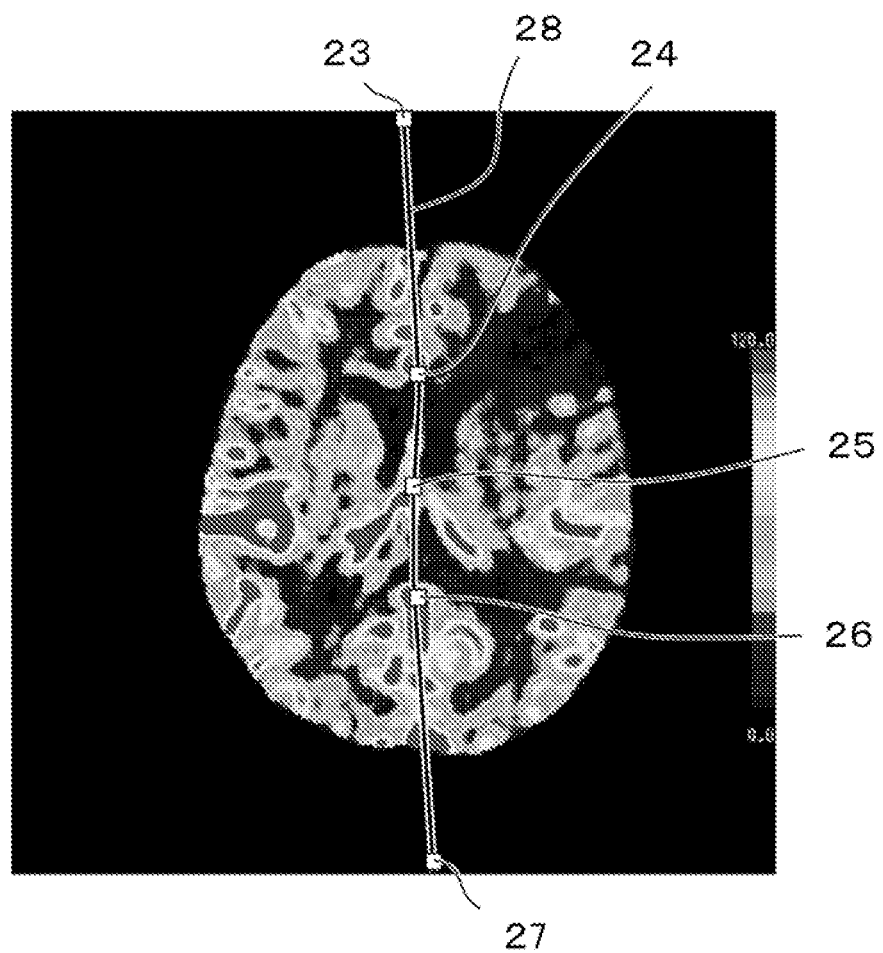
FIG. 6 is a view showing a scene where a centerline is manually drawn.

Moreover, a centerline setting method may be such that: multiple points 23, 24, 25, 26, and 27 are, as shown in FIG. 6, specified manually; and a curve linking the points is set as a centerline 28. Otherwise, after a centerline is tentatively set automatically, the centerline may be manually finely adjusted. However, manual setting is likely to permit invasion of operator's subject. Moreover, a load on an operator increases. Automatic setting is therefore preferable. Herein, a case where a perfusion image is used to set a centerline has been introduced. The employment of an X-ray CT image, an MR image, or any other raw image may sometimes be more preferable because it represents the morphological information on an object. In this case, the raw image may be used to set a centerline.

(Step 205)

Figure 7:
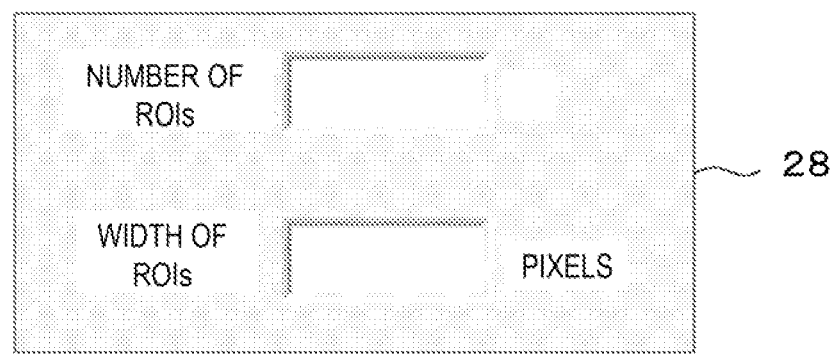
FIG. 7 is a view showing an edit box for use in inputting parameters concerning ROIs.
Figure 8:
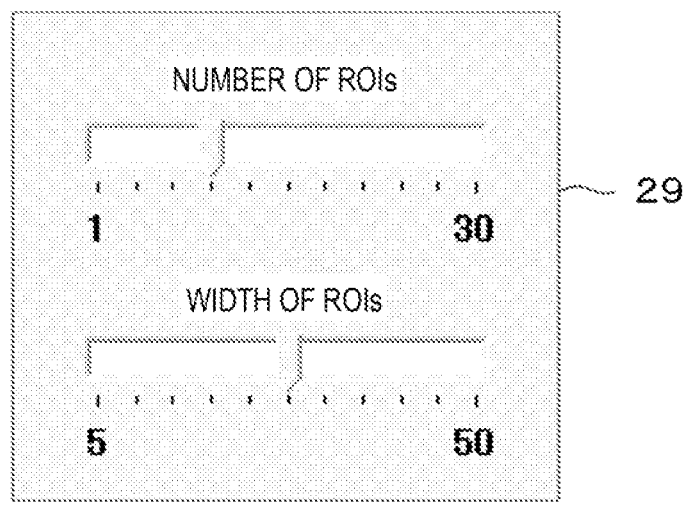
FIG. 8 is a view showing a track bar for use in inputting parameters concerning ROIs.

Thereafter, the operator uses the input means 14 to input parameters (the number of ROIs and the size thereof (a width or a diameter in an embodiment 2 to be described later)) relevant to setting of ROIs to be delineated at a step described below. Specifically, in the present embodiment, an edit box 28 like the one shown in FIG. 7 or a track bar 29 like the one shown in FIG. 8 is displayed on the image display means 3 shown in FIG. 2. The operator uses the edit box or track bar to input the parameters.

(Step 206)

Thereafter, the ROI delineation means 8 delineates ROIs in a perfusion image on the basis of the parameters inputted at step 205. If necessary, ROIs may be delineated not only in the perfusion image but also in a raw image (CT image or MR image) of medical-purpose digital image data. An example of an ROI delineation method will be described below.

<ROI Delineation Method 1>

Figure 9:
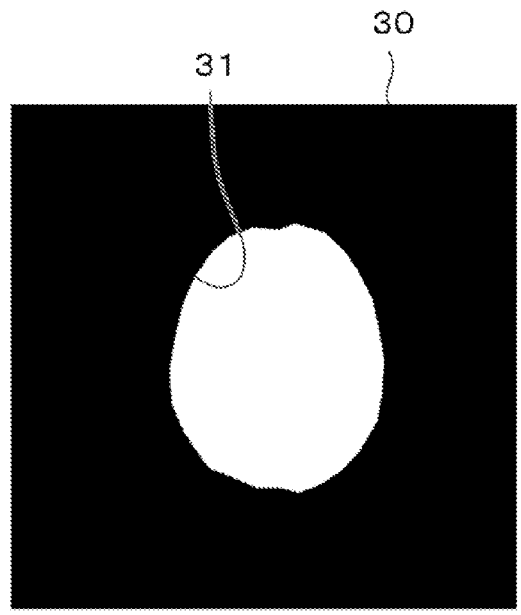
FIG. 9 is a view showing a contracted mask image.

First, an ROI delineation method 1 is a method of rectangularly delineating ROIs in a perfusion image. A region enclosed with a contour 21 of a mask image shown in FIG. 4 and a contour 31 of a contracted mask image 30 shown in FIG. 9 is divided using parting lines, which will be described later, in order to produce ROIs.

Figure 10:
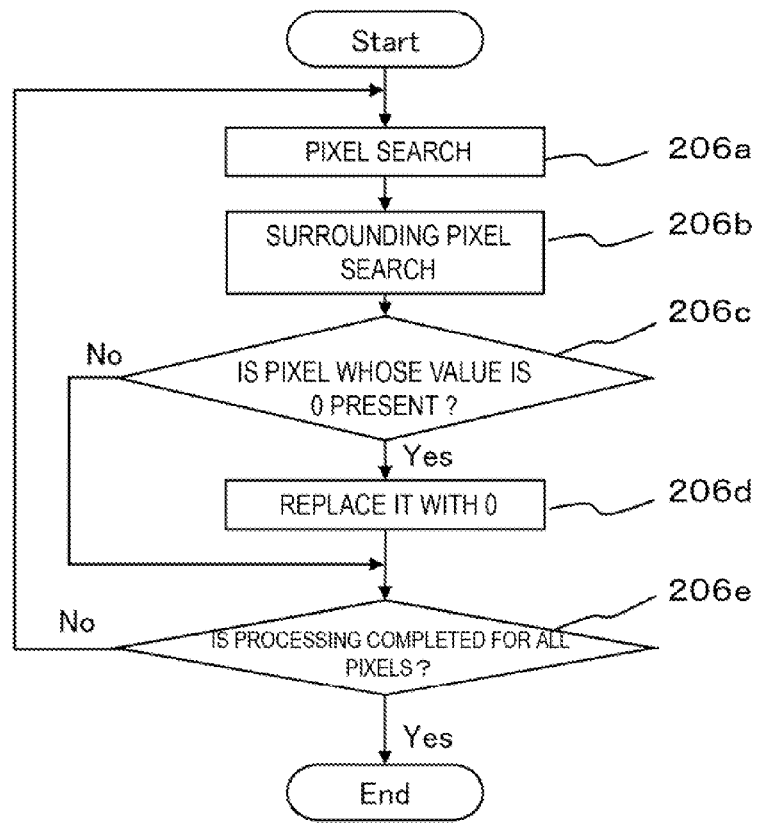
FIG. 10 is a flowchart presenting a processing procedure of a contracted mask image construction method.

To begin with, a contracted mask image construction method in the ROI delineation method 1 will be described below. FIG. 10 is a flowchart presenting a processing procedure of the contracted mask image construction method in the present embodiment which is dealt by the mask construction means 6. Herein, the steps in the flowchart shown in FIG. 10 will be sequentially described below.

(Step 206a)

First, in a mask image obtained as shown in FIG. 4, scanning is performed in a sideways direction from the position of a pixel at a left upper corner, and shifted sequentially downward in order to search pixels whose pixel values are 1.

(Step 206b)

Thereafter, four surrounding pixels (right, left, upper, and lower pixels) are searched for each of the pixels on which a decision is made that the pixel values are 1 (hereinafter, called object pixels).

(Step 206c)

Thereafter, whether the four pixels searched at step 206b include even a pixel whose pixel value is 0 is determined. If even one of the four pixels is a pixel of 0, processing proceeds to step 206d. If none of the four pixels is a pixel of 0, the processing proceeds to step 206e.

(Step 206d)

A pixel that is an object (object pixel) and is determined at step 206c as a pixel whose surrounding pixels includes a pixel whose pixel value is 0 is replaced with 0 in order to construct an image.

(Step 206e)

At this step, a decision is made whether the steps 206a to 206d have been performed on all pixels of a mask image. If the steps have been completed for all the pixels, the processing is terminated. Otherwise, the processing proceeds to step 206a and continues until the processing is completed for all the pixels.

The processing presented in the flowchart of FIG. 10 is implemented by the same number of times as the number of pixels to be contracted from the mask image shown in FIG. 4 into the contracted mask image shown in FIG. 9 (the width of ROIs inputted at step 205 (the diameter of ROIs in an embodiment 2 to be described later): M).

Figure 11:
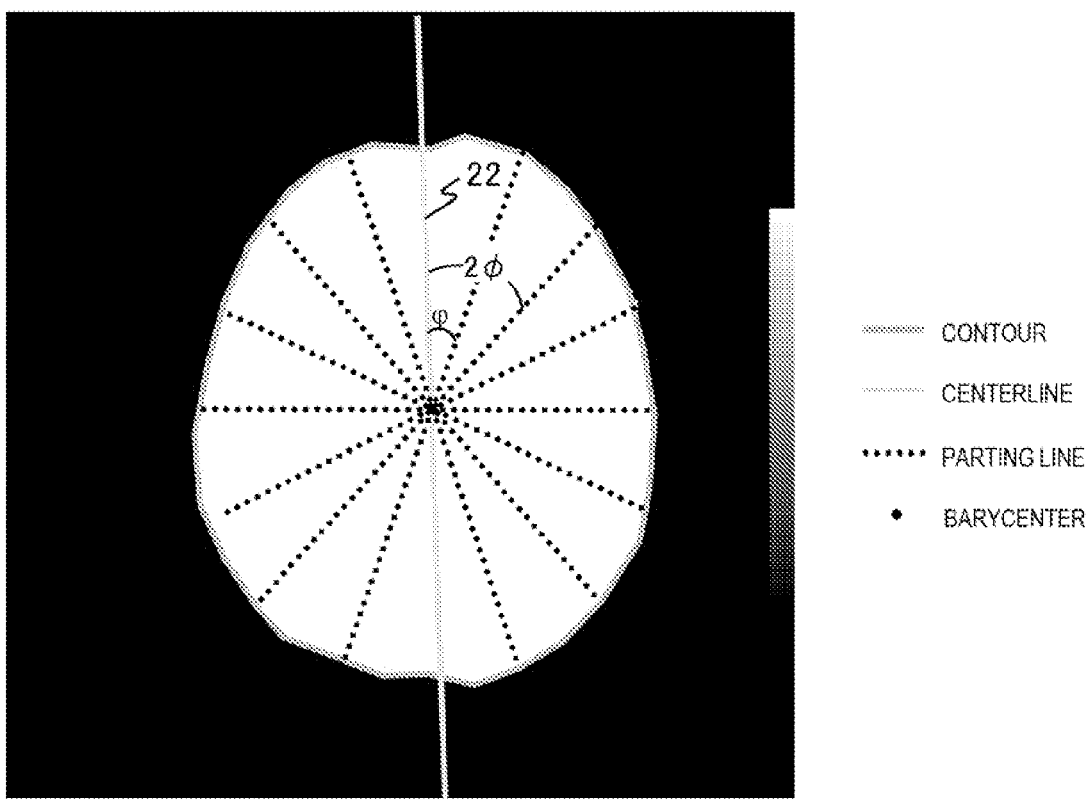
FIG. 11 is a view showing a scene where parting lines are drawn.

Thereafter, a description will be made of a parting line drawing method in the ROI delineation method 1. Herein, what is referred to as a parting line in the present embodiment is a segment drawn by, as shown in FIG. 11, turning a centerline 22 by an angle θ·n with a center point on the centerline 22 in the center of an image as a base point, and traversing it across a brain region from the border on one side of the brain region to the border on the other side thereof. Herein, θ denotes an angle calculated by dividing 180 by N, and n denotes an integer ranging from 0 to N−1.

The parameter M in the above description indicates the width in a radial direction of ROIs with the number of pixels by which a contracted mask image is contracted with respect to a mask image by executing the processing of the flowchart of FIG. 10. N indicates the number of ROIs to be set in the right half or left half of a brain image. The parameters are inputted at step 205 in the flowchart in FIG. 2. For example, assuming that the width in a radial direction of ROIs is M pixels and the number of ROIs in the right half or left half of the brain image is eight, a perfusion image to which delineated ROIs are applied is as shown in FIG. 12.

Figure 12:
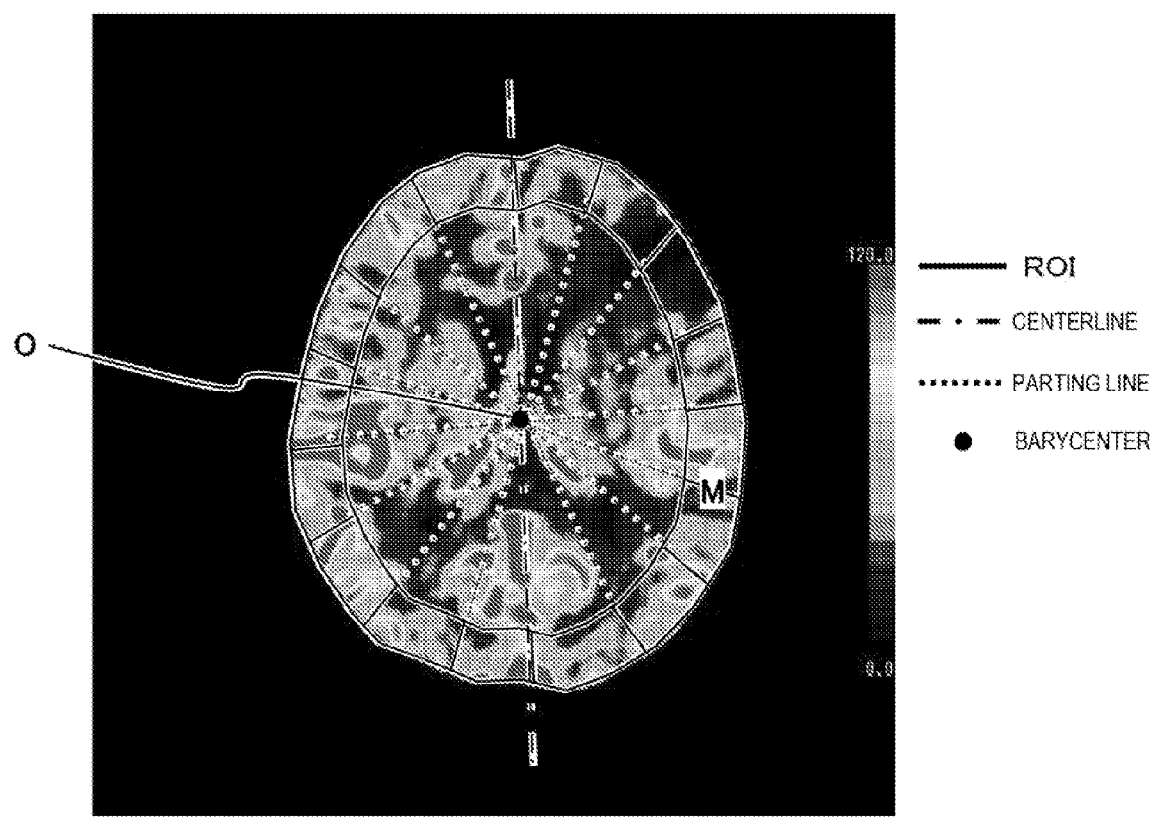
FIG. 12 is a view showing a perfusion image to which delineated ROIs are applied.

In FIG. 12, the widths in a radial direction of all ROIs are identical. However, the size of an object's head may be different between the left hemisphere and the right hemisphere because of surgery or the like. In this case, the lengths of the widths in the radial direction of ROIs may be adjusted in line with the sizes of the left and right head parts. For example, assuming that $S_L$ denotes the area in an image of the left-brain side head part and $S_R$ denotes the area in the image of the right-brain side head part, when the width in the radial direction of ROIs on the left brain side is set to M, the width in the radial direction of ROIs on the right brain side should be $M \times S_R/S_L$.

(Step 207)

Thereafter, the intra-ROI information analysis means 9 analyzes data of a perfusion image for each of ROIs delineated at step 206. More particularly, at this step, the intra-ROI information analysis means 9 calculates a mean value or a standard deviation, etc. of pixel value data of the perfusion image within each ROI. Now, a construction method for an ROI mask needed to analyze intra-ROI information will be described below.

<ROI Mask Construction 1>

Figure 13:
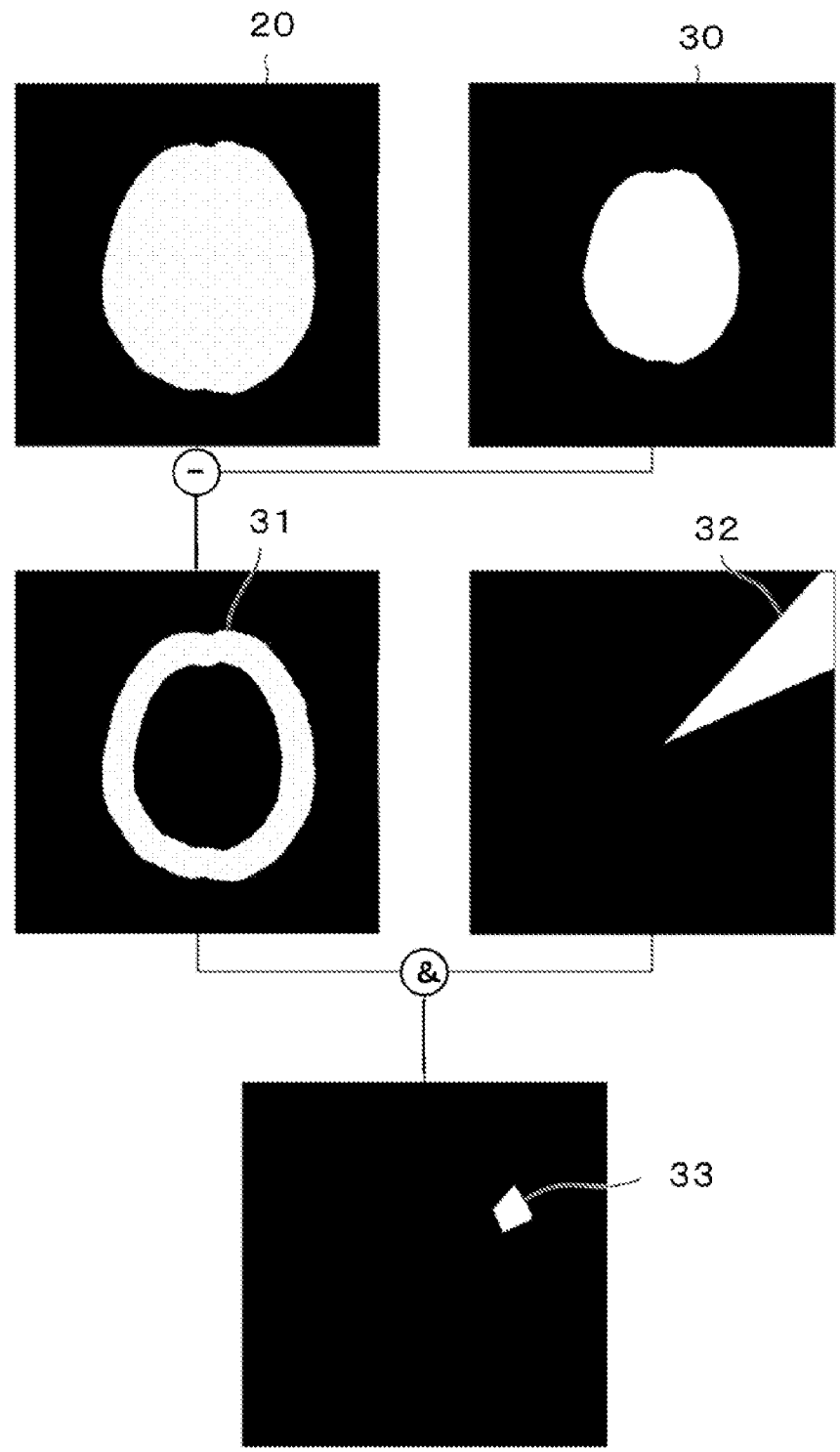
FIG. 13 includes views showing a scene where an ROI mask is constructed.

In analysis of data of a perfusion image at the present step, construction of an ROI mask is performed prior to calculation of blood-flow parameters. For example, when ROIs are rectangularly delineated as they are in the ROI delineation method 1, subtraction between the mask image shown in FIG. 4 and the contracted mask image shown in FIG. 9 is performed first in order to construct an image 31 shown in FIG. 13. Further, the pixel values in a region enclosed with two adjoining parting lines are set to 1, and the pixel values in the other regions are replaced with 0. Thus, a parting region mask 32 is constructed. An AND operation is performed in order to extract an area in which both the image 31 and parting area mask 32 have the pixel value of 1, whereby an ROI mask 33 is constructed.

(Step 208)

Thereafter, the left-and-right comparison means 10 compares the left and right ROIs, which are disposed at anatomically laterally symmetrical positions, with each other in terms of an analytic value of data of a perfusion image obtained at step 207. A method of comparing the left and right ROIs with each other will be described below.

<Left-and-Right ROI Comparison Method>

Figure 14:
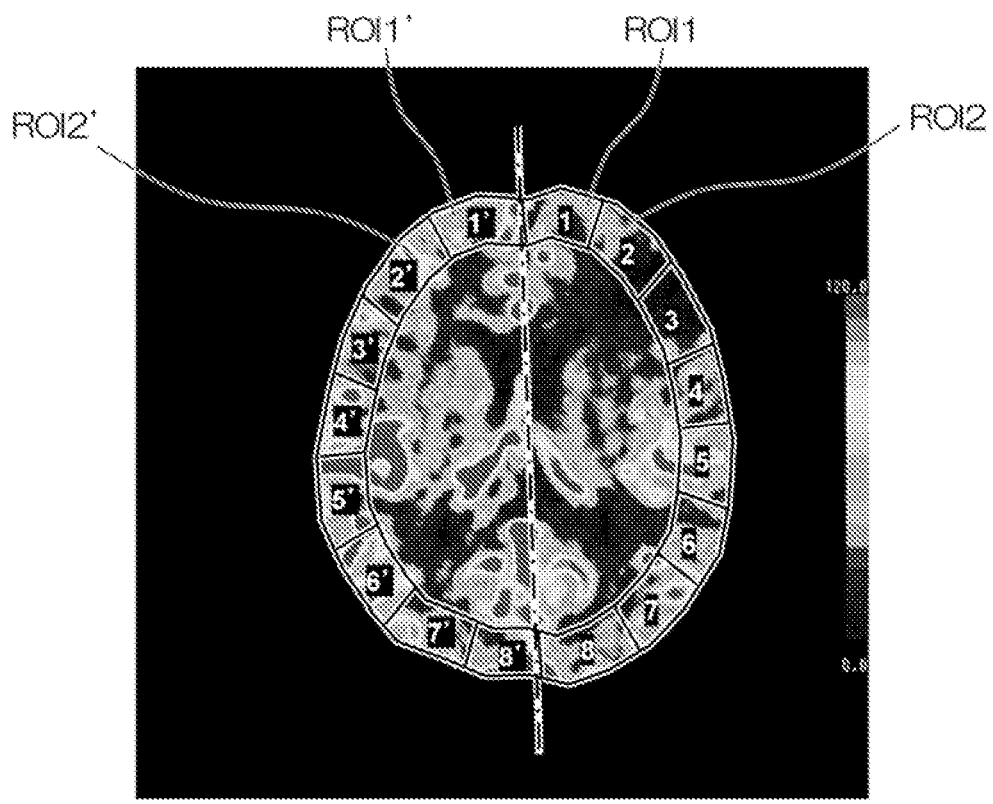
FIG. 14 is a view showing a scene where ROIs disposed at anatomically symmetric positions are compared with each other.

Left-and-right comparison is to compare ROIs, which are located at anatomically symmetrical positions, with each other. FIG. 14 shows the positional relationship between ROIs to be compared with each other. In FIG. 14, ROIs bearing the same numeral such as 1 and 1', 2 and 2', or the like are ROIs located at anatomically symmetrical positions. The n-th uppermost left and right ROIs are compared with each other. Herein, n denotes an integer ranging from 1 to N, and N denotes the number of ROIs that is specified by an operator and that is set in each of the left and right hemispheres of the brain.

Left-and-right comparison may be comparison to be performed by obtaining a left-and-right ratio between mean values of absolute values of pixel values in the left and right ROIs in a perfusion image, or by obtaining a left-and-right difference between mean values of absolute values of pixel values in the left and right ROIs. However, in analysis of a cerebral perfusion image of an X-ray CT apparatus or an MR apparatus, the stability and reliability of quantitative values have not been established to date. The accuracy in assessment is not guaranteed. Therefore, for objective assessment, the left-and-right ratio would be preferable.

(Step 209)

Thereafter, an operator uses the input means 14 to input an assessment parameter to be used to determine whether a blood-flow abnormality has occurred in an ROI that is an object. More particularly, A is inputted as an index (threshold) based on which a decision is made that when ROIs located at anatomically laterally symmetrical positions are compared with each other, if the left-and-right ratio between analytic values (mean values, standard deviations, or the like) in the left and right ROIs is equal to or larger than a what %, the compared ROI is abnormal. Moreover, B is inputted as an index (threshold) based on which a decision is made that if the left-and-right difference between absolute values of blood-flow parameter values is equal to or larger than a whatever value, the compared ROI is abnormal. For inputting, the edit box may be used as it is at step 205, or the track bar may be used.

(Step 210)

Thereafter, the seriousness assessment means 11 assesses based on comparison data (value of a left-and-right ratio or left-and-right difference) obtained at step 208 and whichever of assessment parameters inputted for blood-flow abnormality determination at step 209 is larger whether a blood-flow abnormality has occurred in each of ROIs. An example of display of the results of assessment will be described below.

<Display of the Results of Assessment>

Figure 15:
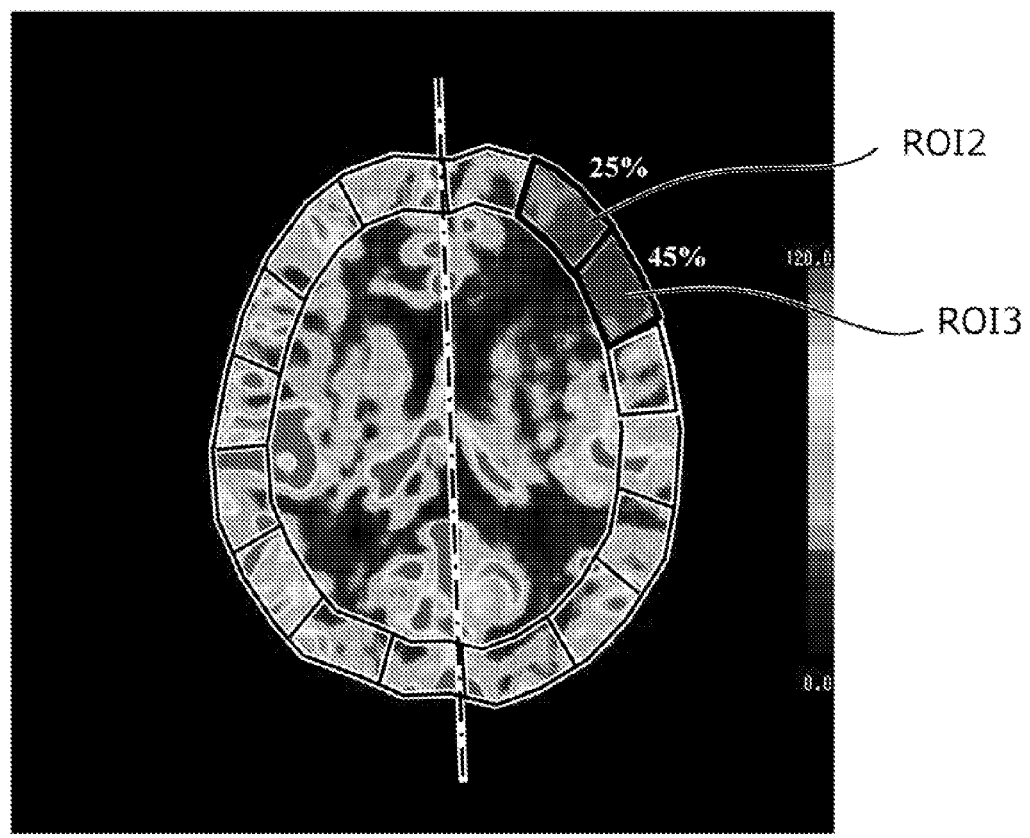
FIG. 15 is a view intended to display which of ROIs is an ROI in which blood-flow abnormality is present.

Next, an example of display of the results of assessment at step 210 will be described. When a ratio for determination of a blood-flow abnormality in an ROI that is an object is inputted as a left-and-right ratio of A % or more at step 209, an ROI a ratio of which to an ROI located at an opposite symmetrical position is equal to or larger than A % is, as shown in FIG. 15, translucently painted out in order to display an abnormality (lesion) (ROI2 and ROI3 in the example of FIG. 15). At this time, not only the inside of the frame of an ROI is translucently painted out but also the inside of the frame may be displayed in any color or the frame or the inside of the frame may be flickered. Moreover, a numerical value of a result of assessment or the like may be indicated in an image. In FIG. 15, the left-and-right ratio is indicated for only ROIs in which a blood-flow abnormality is recognized. The left-and-right ratio may be indicated for all ROIs or may be indicated for a desired ROI alone. Moreover, if necessary, a blood-flow parameter of a mean value or a standard deviation in an ROI, or a mean value, a standard deviation or a left-and-right difference between laterally symmetrical ROIs may be indicated.

(Step 211)

Based on the results obtained by the above step, an operator decides whether at least one of a centerline, parameters concerning setting of ROIs, and an assessment parameter should be modified in order to perform reassessment. If reassessment is performed, the parameters are modified, and step 204 and subsequent steps, step 205 and subsequent steps, or step 209 and subsequent steps are re-executed.

(Step 212)

If a decision is made at step 211 that reassessment is not needed, the results of assessment obtained by step 210 are stored. At this time, the number and the positions of ROIs in which an a blood-flow abnormality has presumably occurred, analytic values of blood-flow parameters of the ROIs, the left-and-right ratios and left-and-right differences between the ROIs and ROIs located at anatomically symmetrical positions (for example, opposite positions with a centerline between them), and a perfusion image on which the ROIs are superposed are preferably stored.

According to the above embodiment, parting lines are drawn with the barycenter of a mask image of a head image as a center, and multiple ROIs are set in a region, which extends inward by a predetermined distance from the outer circumference of the mask image so that they will be segmented by the parting lines. Consequently, ROIs can be set at more objectively accurate positions than they are set manually. According to the present embodiment, at what position an affected part lies, how many affected parts are present, and to what degree the affected parts are grave can be objectively assessed. The comprehensive seriousness of an object's pathological state can be assessed.

Embodiment 2

Next, an ROI delineation method in an embodiment 2 of the invention, and an ROI mask construction method in the method will be described below.

<ROI Delineation Method 2>

A method presented as the ROI delineation method 2 is, unlike the method presented as the ROI delineation method 1, a method of designating circular ROIs.

First, for setting of circular ROIs, parting lines similar to those employed in the method shown in FIG. 11 and included in the ROI delineation method 1 are set. Now, θ denotes an angle expressed by 180/(N+1) on the assumption that N denotes the number of circular ROIs to be set in a half region of the brain.

Figure 16:
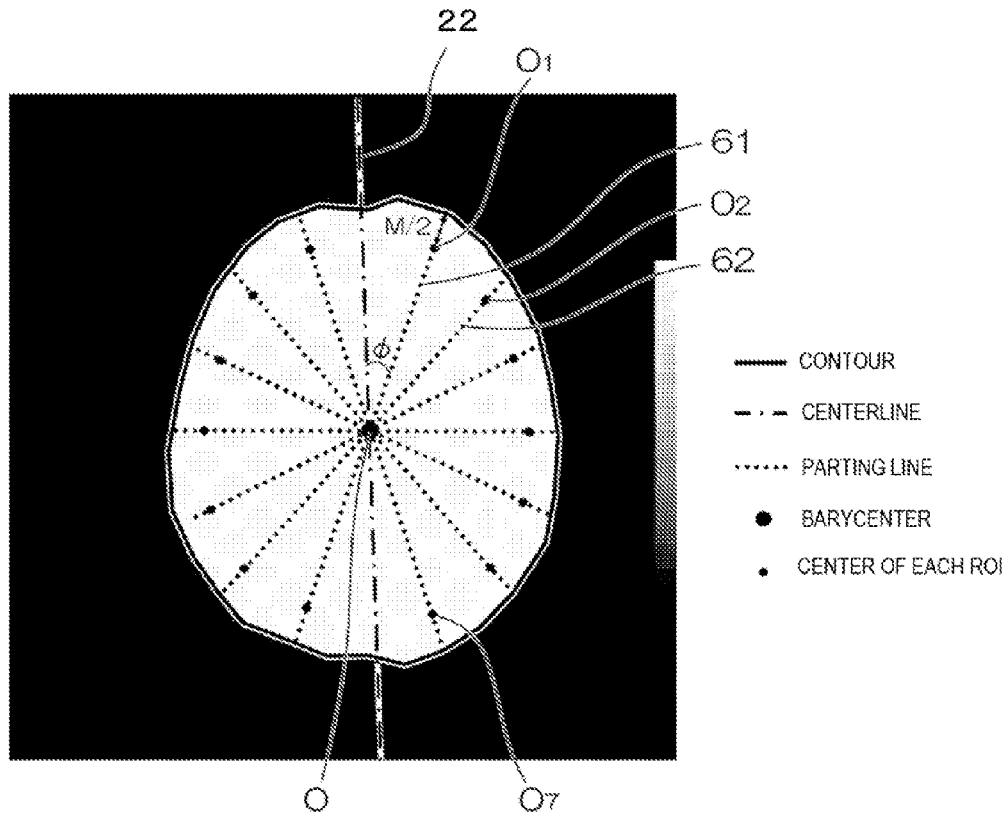
FIG. 16 is a view showing a scene where center points of ROIs are disposed according to an ROI delineation method 2.

Thereafter, if an operator inputs M pixels as the diameter of circular ROIs at step 205 in the embodiment 1, the center points $O_1$ to $O_N$ of the circular ROIs are, as shown in FIG. 16, disposed inward by M/2 pixels from the contour of a mask image.

Figure 17:
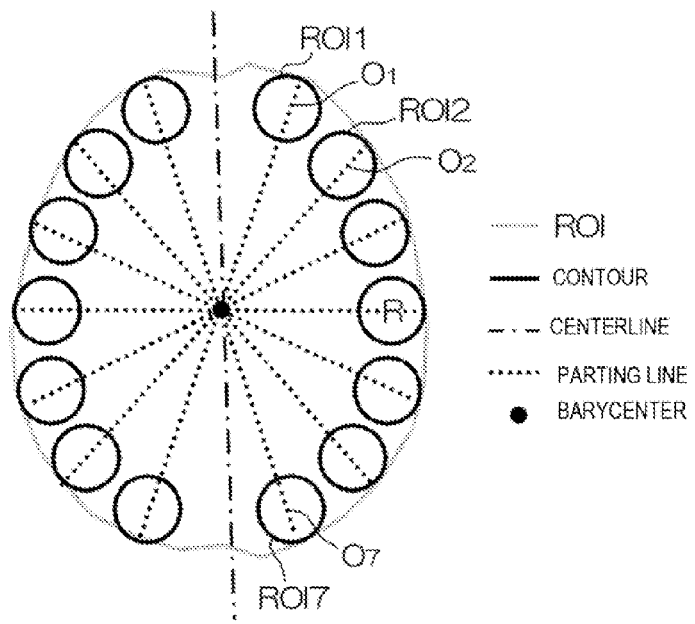
FIG. 17 is a diagram showing a scene where ROIs are delineated according to the ROI delineation method 2.
Figure 18:
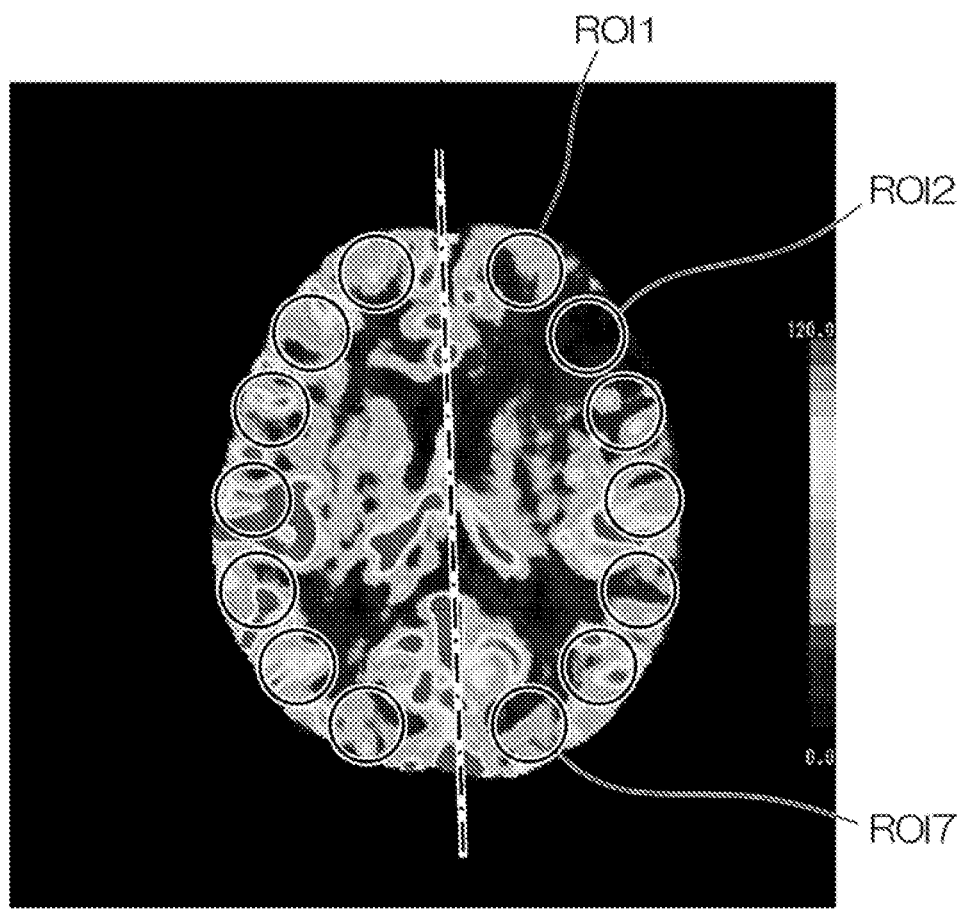
FIG. 18 is a view of ROIs delineated according to the ROI delineation method 2 and superposed on a perfusion image.
Figure 19:
FIG. 19 is a view of ROIs produced with the diameter thereof made a bit smaller and with the number of ROIs set to 15, and superposed on a perfusion image.

At this time, the ROIs are delineated as shown in FIG. 17. When the ROIs are superposed on a perfusion image and displayed, they appear as shown in FIG. 18. Moreover, assuming that the diameter of ROIs is set to R pixels that is a bit smaller value, and the number of ROIs is set to 15, a graphic having constructed ROIs superposed on a perfusion image appears as shown in FIG. 19.

In the example of FIG. 18, a pixel superposed to be included in multiple ROIs is not present, but a considerable number of pixels of cerebral neocortexes that is not included in the ROIs is present. On the other hand, in the example of FIG. 19, pixels superposed to be included in multiple ROIs are present, and almost all the pixels of the cerebral neocortexes are found to be included in the ROIs. However, in clinical practice, almost all the cerebral neocortexes should desirably be regarded as objects of assessment. Therefore, the ROIs should preferably be set as they are shown in FIG. 19.

Moreover, the present embodiment is concerned with a case where the diameters of ROIs are identical to one another. However, the size of an object' head may be different between the left hemisphere and right hemisphere thereof because of surgical operation. In this case, the width in a radial direction of ROIs may be adjusted based on the sizes of the left and right head parts. For example, assuming that $S_L$ denotes the area in an image of the left-brain side head part and $S_R$ denotes the area in the image of the right-brain side head part, when the diameter of the ROIs on the left-brain side is M, the diameter of the ROIs on the right-brain side should be set to $M \cdot S_R/S_L$.

<ROI Mask Construction 2>

In ROI mask construction in the present embodiment, the outer circumferences of circular ROIs are plotted according to an equation of a circle, and the insides thereof are painted out.

Even in the present embodiment, parting lines are drawn with the barycenter of a mask image of a head image as a center, and multiple circular ROIs are set with the positions, which lies a predetermined distance inward from the outer circumference of the mask image, as the centers of the ROIs. Therefore, the ROIs can be set at more objectively accurate positions than they are set manually. According to the present embodiment, at what positions affected parts lie, how many affected parts are present, and to what extent the affected parts are grave can be objectively assessed. The comprehensive seriousness of an object's pathological state can be assessed.

Embodiment 3

Next, FIG. 20 shows an example of display of the results of assessment made by the seriousness assessment means 11 in an embodiment 3 of the invention. FIG. 20 shows an example of display of the results of assessment made at step 210 in the embodiment 1. Based on the number of ROIs in which a blood-flow abnormality is detected and the degrees of the abnormalities (for example, what-percents or more the ratio between left and right opposite ROIs is), the seriousness of an object's pathological state is scored. In FIG. 20, the leftmost column indicates the left-and-right ratio between left and right opposite ROIs by classifying it into some ranges. The second leftmost column indicates a mark or a grade, which signifies how mild seriousness is, in association with each range of left-and-right ratios. The higher the mark is (as the mark approaches 5), the milder the seriousness is. The third leftmost column indicates the number of ROIs included in each range of left-and-right ratios between ROIs. The rightmost column indicates a product of the mark (A), that is, the grade and the number of ROIs (B) in association with each range of left-and-right ratios. The sum total of the numerals entered in the right most column is calculated. As the sum total (score) is smaller, a blood-flow abnormality is decided to be graver. This may be used as data for determining a future therapeutic policy. A technique for scoring the seriousness of a blood-flow abnormality is not limited to the example in FIG. 20, but an arbitrary technique will do. Preferably, the grade is varied depending on the left-and-right ratio, and seriousness is scored by multiplying the grade by the number of associated ROIs. Moreover, if what therapeutic policy would be taken in relation to what sum total (score) is attained under predetermined conditions for ROI setting is determined prior to examination, the present embodiment would be effectively applied.

Embodiment 4

Next, FIG. 21 shows an example of display of the results of assessment made by the seriousness assessment means 11 in an embodiment 4 of the invention. FIG. 21 shows an example of display of the results of assessment made at step 210 in the embodiment 1. A mean value of perfusion image data, a standard deviation, a left-and-right mean value ratio, and a left-and-right mean value difference are listed in the form of a table in association with the position of each pair of ROIs. When the analytic values and left-and-right comparison data items are displayed in the form of a table, an operator could more practically grasp the degree of a lesion in each ROI.

The invention is not limited to the aforesaid embodiments but can be varied in various manners without a departure from the gist of the invention. For example, in the aforesaid embodiments, examples of analytically assessing a perfusion image of an object's head image have been presented. However, the invention is not limited to the object's head but can be applied to assessment to be performed by designating ROIs at laterally symmetrical positions in any other organ such as the laterally symmetrical lung. Moreover, the invention can be applied not only to the perfusion image but also to an ordinary image. Moreover, needless to say, not only ROIs are set at linearly symmetrical positions in an object's organ and compared with each other but also ROIs may be set at rotationally symmetrical positions in an organ having rotational symmetry, and compared with each other. Moreover, in the embodiment 2, when circular ROIs are set, the centers of the circles are disposed on respective parting lines. Alternatively, needless to say, each of the circular ROIs may be disposed in a region enclosed with adjoining parting lines so that the tangents on the ROI will be the parting lines.

The invention claimed is:

1. An image analysis method performed by an image processing apparatus to analyze medical-purpose image data corresponding to an image of an object's organ having an anatomically symmetric shape, wherein said image analysis method performed by said image processing apparatus comprises:

(1A) a step of inputting the medical-purpose image data corresponding to the image of the organ;

(1B) a step of generating mask image data which collectively express a mask image corresponding to a region of the organ, based on processing the image data corresponding to the image of the organ;

(1) a step of determining, based on the image data, and designating, a centerline of the organ in the image constituted by the image data;

(2) a step of setting N-1 parting lines based on processing of the mask image data and the centerline designated in the step (1), wherein N is an integer greater than two, the N-1 parting lines intersect at a barycenter of the mask image corresponding to a region of the organ and form an angle θ·n with the centerline, wherein θ is an angle calculated by dividing 180° by N, and n denotes an integer ranging from 0 to N-1;

(3) a step of setting automatically a plurality, or more than one pair, of regions of interest at symmetrical opposite positions, based on processing of the mask image data obtained in step (1B) and the parting lines set in the step (2);

(4) a step of generating an analytic value of the image data in each of the regions of interest, based on processing of the image data in each of the regions of interest set in the step (3); and (5) a step of assessing the state of the object according to a degree of a difference in the analytic value between the opposite regions of interest.

2. The image analysis method according to claim 1, further comprising:

(8) a step of obtaining a position of the barycenter of the mask and a slope of a principal axis of inertia on the basis of the mask indicated in the mask image, wherein:

the mask image is constructed in step (6) by binarizing a region in the image in which the organ is included, and at the step (1), the centerline is set based on the position of the barycenter and the slope of the principal axis of inertia.

3. An image processing apparatus that analyzes medical-purpose image data corresponding to an image of an object's organ having an anatomically symmetric shape, the image processing apparatus comprising:

an image data reader configured to acquire the medical-purpose image data of the organ;

a memory coupled with the image data reader to receive the medical-purpose image data therefrom and configured to store the medical-purpose image data;

an input device;

a processor coupled with said input device and said memory to respond to input conditions set at the input device and to retrieve the medical-purpose image data from the memory and configured to process the retrieved medical-purpose image data, to generate analytic information by performing:
  processing the medical-purpose image data corresponding to the image of the organ to generate mask image data which collectively express a mask image corresponding to a region of the organ;
  processing the image data to determine and designate a centerline of the organ in the image constituted by the image data, wherein said anatomical symmetric shape of the object's organ is a shape laterally symmetric with respect to said centerline;
  processing the mask image data and the centerline to set N-1 parting lines, wherein N is an integer greater than two, the N-1 parting lines intersect at a barycenter of the mask image corresponding to a region of the organ and form an angle θ·n with the centerline, wherein θ is an angle calculated by dividing 180° by N, and n denotes an integer ranging from 0 to N-1;
  processing the mask image data and the parting lines to automatically set a plurality, or more than one pair, of regions of interest at symmetrical opposite positions;
  processing the image data in each of the regions of interest to generate an analytic value of the image data in each of the regions of interest; and
  assessing the state of the object according to a degree of a difference in the analytic value between the opposite regions of interest; and
a display coupled with the memory to display an image based on the image data from the memory and to display the analytic information corresponding to the object or the organ.

* * * * *